United States Patent [19]

Tahara et al.

[11] Patent Number: 4,820,703

[45] Date of Patent: Apr. 11, 1989

[54] PAF-ANTAGONISTIC THIENOTRIAZOLODIAZEPINE COMPOUNDS AND PHARMACEUTICAL USES THEREOF

[75] Inventors: Tetsuya Tahara; Minoru Moriwaki, both of Oita; Masao Abe; Shuji Yuasa, both of Fukuoka, all of Japan

[73] Assignee: Yoshitomi Pharmaceutical Industries Ltd., Japan

[21] Appl. No.: 121,834

[22] Filed: Nov. 17, 1987

[30] Foreign Application Priority Data

| | | | |
|---|---|---|---|
| Nov. 17, 1986 | [JP] | Japan | 61-273395 |
| Apr. 15, 1987 | [JP] | Japan | 62-94058 |
| Sep. 4, 1987 | [JP] | Japan | 62-222721 |

[51] Int. Cl.⁴ .................. C07D 495/12; C07D 495/04; A61K 31/55

[52] U.S. Cl. .................. 514/220; 540/560; 540/568

[58] Field of Search .................. 540/560; 514/220

[56] References Cited

U.S. PATENT DOCUMENTS

| | | | |
|---|---|---|---|
| 3,904,641 | 9/1975 | Nakanishi | 540/560 |
| 4,155,913 | 5/1979 | Hellerbach | 540/560 |
| 4,199,588 | 4/1980 | Weber | 540/560 |
| 4,201,712 | 5/1980 | Weber | 540/560 |

FOREIGN PATENT DOCUMENTS 0194416 1/1986 European Pat. Off. .

OTHER PUBLICATIONS

Teresawa, Japanese Journal of Pharmacology, No. 4, vol. 44, pp. 381–391, Aug. 1987.

Yoshitomi Pharm. Co., Chemical Abstracts, vol. 94, p. 583, Abstract No. 47337w (1981).

*Primary Examiner*—Mark L. Berch

*Attorney, Agent, or Firm*—Sughrue, Mion, Zinn, Macpeak, and Seas

[57] ABSTRACT

A thienotriazolodiazepine compound of the formula:

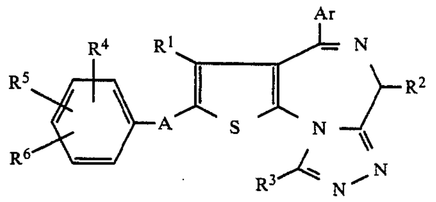

wherein A is alkylene or substituted alkylene and each other symbol is as defined in the specification and a pharmaceutically acceptable acid addition salt thereof, and pharmaceutical uses thereof.

Said compounds exhibit PAF-antagonistic activity and are useful for the prevention or treatment of various PAF-induced diseases.

5 Claims, No Drawings

PAF-ANTAGONISTIC THIENOTRIAZOLODIAZEPINE COMPOUNDS AND PHARMACEUTICAL USES THEREOF

BACKGROUND OF THE INVENTION

1. Field of the Invention

The present invention relates to novel and pharmaceutically useful thienotriazolodiazepine compounds and pharmaceutically acceptable acid addition salts thereof, and pharmaceutical uses thereof.

2. Description of the Prior Art

Certain s-triazolo[3,4-c]thieno[2,3-e][1,4]diazepine compounds represented by 6-(o-chlorophenyl)-8-ethyl-1-methyl-4H-s-triazolo[3,4-c]thieno[2,3-e][1,4]diazepine [hereinunder referred to as Etizolam (Recommended INN)] are known to exhibit useful pharmacological activities against the central nervous system such as antianxiety or anticonvulsant activities as disclosed in U.S. Pat. No. 3,904,641.

Japan. J. Pharmacol., vol. 44, p. 381-391 (1987) discloses that Etizolam exhibits antagonistic activity on platelet-activating factor (hereinunder referred to as PAF), and further EP-A 194416 discloses that s-triazolo[3,4-c]thieno[2,3-e][1,4]diazepine-carboxylic acid amide compounds also exhibit antagonistic activity on PAF.

Benveniste et al. found a factor which strongly induced platelet aggregation from rabbit basophils, and named as platelet-activating factor (PAF) in 1972. Hanahan et al. identified that the factor was phosphoglyceride of alkyl ether type having acetyl group in the 2-position, i.e. 1-O-hexadecyl or octadecyl-2-acetyl-sn-glyceryl-3-phosphorylcholine, in 1980.

The physiological roles of PAF have been intensively investigated, and it has been known that PAF was an important factor of various physiological reactions inclusive of platelet aggregation, reduction in blood pressure, immediate allergic reaction, contraction of smooth muscle, inflammation, pain, edema, as well as alteration in the respiratory and circulatory systems.

Therefore, PAF-antagonistic activity-possessing compounds are considered to be very useful for various PAF-induced diseases such as inflammatory diseases, allergic diseases, anaphylactic shocks, septic shocks, vascular diseases as DIC, myocardial diseases, asthma, pulmonary edema, adult respiratory diseases.

Recently, certain s-triazolo[3,4-c]thieno[2,3-e][1,4]diazepine compounds have been shown to exhibit PAF-antagonistic activity as described above. However such compounds are not sufficient in view of the separation from the effect on the central nervous system, the potency, the effectiveness by the oral administration or the duration of activity. Therefore, it is desirable to provide potent PAF-antagonistic thienotriazolodiazepine compounds which possess not only effectiveness by oral administration and long-lasting effect, but also less inhibitory effect on the central nervous system.

SUMMARY OF THE INVENTION

The present invention provides a new series of PAF-antagonistic thieno[3,2-f][1,2,4]triazolo[4,3-a][1,4]diazepine compounds substituted by an aralkyl group in the 2-position, which are effective and long-acting by the oral administration, and moreover long-acting, and show less inhibitory action in the central system as sedative activity or muscle relaxation activity, and pharmaceutical uses thereof.

DETAILED DESCRIPTION OF THE INVENTION

The present invention relates to thienotriazolodiazepine compounds of the formula:

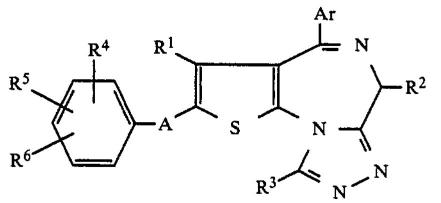

(I)

wherein Ar is pyridyl, phenyl or substituted phenyl by one to three substituents optionally selected from the group consisting of halogen, hydroxy, trifluoromethyl, straight or branched chain alkyl having 1 to 5 carbon atoms and straight or branched chain alkoxy having 1 to 5 carbon atoms, A is alkylene having 1 to 8 carbon atoms or substituted alkylene having 1 to 8 carbon atoms by straight or branched chain alkyl having 1 to 5 carbon atoms, $R^1$ is hydrogen or straight or branched chain alkyl having 1 to 5 carbon atoms, $R^2$ and $R^3$ are the same or different and each is hydrogen, trifluoromethyl or straight or branched chain alkyl having 1 to 5 carbon atoms, and $R^4$, $R^5$ and $R^6$ are the same or different and each is hydrogen, halogen, hydroxy, trifluoromethyl, straight or branched chain alkyl having 1 to 8 carbon atoms, straight or branched chain alkyl having 1 to 8 carbon atoms substituted by trifluoromethyl, straight or branched chain alkoxy having 1 to 8 carbon atoms, phenyl, phenoxy, aralkyl, aralkyloxy, or substituted phenyl, phenoxy, aralkyl or aralkyloxy by one to three substituents optionally selected from the group consisting of halogen, hydroxy, straight or branched chain alkyl having 1 to 5 carbon atoms, trifluoromethyl and straight or branched chain alkoxy having 1 to 5 carbon atoms on the aromatic ring, and pharmaceutically acceptable acid addition salts thereof. The present invention also provides a pharmaceutical composition, a therapeutical method, and a use for the prevention or treatment of various PAF-induced diseases.

In the definitions of the above symbols, halogen includes chlorine, bromine, fluorine and iodine; straight or branched chain alkyl having 1 to 5 carbon atoms includes, for example, methyl, ethyl, n-propyl, isopropyl, n-butyl, isobutyl, tert-butyl, n-pentyl, isopentyl, tert-pentyl or 1-methylbutyl; straight or branched chain alkoxy having 1 to 5 carbon atoms includes, for example, methoxy, ethoxy, n-propoxy, isopropoxy, n-butoxy, isobutoxy, tert-butoxy, n-pentyloxy, isopentyloxy, tert-pentyloxy or 1-methylbutyloxy; pyridyl includes 2-pyridyl, 3-pyridyl and 4-pyridyl; alkylene having 1 to 8 carbon atoms means straight-chain alkylene and includes, for example, methylene, ethylene, trimethylene, tetramethylene, pentamethylene, hexamethylene, heptamethylene, or octamethylene, and substituted alkylene having 1 to 8 carbon atoms by straight or branched chain alkyl having 1 to 5 carbon atoms means the substituted alkylene by the alkyl on the same or different carbon atom or atoms such as methylmethylene, propylene, methyltrimethylene, dimethylethylene, dimethyltetramethylene, ethylethylene or dimethyltrimethylene; straight or branched chain alkyl having 1 to 8 carbon atoms includes, for example, methyl, ethyl, n-propyl, isopropyl, n-butyl, isobutyl, tert-butyl, n-pentyl, isopentyl, 1-methylbutyl, n-hexyl, 1-methylpentyl, n-heptyl, 4-methylhexyl, 1-ethylpentyl, 1,4-dimethylpentyl, n-octyl, 6-methylheptyl or 2-ethylhexyl, straight or branched chain alkyl having 1 to 8 carbon atoms substituted by trifluoromethyl includes, for example, 2,2,2-trifluoroethyl, 3,3,3-trifluoropropyl, 1-trifluoromethylethyl or 2-trifluoromethylpropyl; straight or branched chain alkoxy having 1 to 8 carbon atoms includes, for example, methoxy, ethoxy, n-propoy, isopropoxy, n-butoxy, isobutoxy, tert-butoxy, n-pentyloxy, isopentyloxy, n-hexyloxy, n-heptyloxy, 1-propylbutoxy, n-octyloxy, 5-methylhexyloxy, 2-ethylhexyloxy or 1,6-dimethylhexyloxy; aralkyl includes, for example, benzyl, 1-phenyletgyl, 2-phenylethyl, 3-phenylpropyl or 4-phenylbutyl; and aralkyloxy includes, for example, benzyloxy, 2-phenylethoxy, 3-phenylpropoxy or 4-phenylbutoxy; and substituted phenyl phenoxy, aralkyl or aralkyloxy by one to three substituents optionally selected from the group consisting of halogen, hydroxy, straight or branched chain alkyl having 1 to 5 carbon atoms, trifluoromethyl and straight or branched chain alkoxy having 1 to 5 carbon atoms includes, for example, 2-chlorophenyl, 2-bromophenyl, 3-fluorophenyl, 2,3-dichlorophenyl, 4-hydroxyphenyl, 2-methylphenyl, 4-methylphenyl, 3-ethylphenyl, 4-propylphenyl, 4-isopropylphenyl, 4-butylphenyl, 4-tert-butylphenyl, 4-pentylphenyl, 2,4-dimethylphenyl, 2-trifluoromethylphenyl, 3-trifluoromethylphenyl, 2-methoxyphenyl, 4-methoxyphenyl, 3-ethoxyphenyl, 2-propoxyphenyl, 4-butoxyphenyl, 2,4-dimethoxyphenyl, 3,4,5-trimethoxyphenyl, 2-chlorophenoxy, 2,3-dichlorophenoxy, 4-hydroxyphenoxy, 2-methylphenoxy, 4-butylphenoxy, 2,4-dimethylphenoxy, 2-trifluoromethylphenoxy, 2-methoxyphenoxy, 4-methoxyphenoxy, 2,4-dimethoxyphenoxy, 3,4,5-trimethoxyphenoxy, 2-chlorobenzyl, 2,3-dichlorobenzyl, 4-hydroxybenzyl, 2-methylbenzyl, 2-trifluoromethylbenzyl, 4-methoxybenzyl, 3,4,5-trimethoxybenzyl, 2-(2-chlorophenyl)ethyl, 2-chlorobenzyloxy, 2,4-dimethylbenzyloxy, 2-trifluoromethylbenzyloxy, 3,4,5-trimethoxybenzyloxy, 2-(2-chlorophenyl-)ethoxy, 2-(2,4-dimethylphenyl)ethoxy.

The pharmaceutically acceptable acid addition salts of the compounds of formula (I) includes, for example, salts with an inorgaic acid such as hydrochloride, sulfurate, phosphate, hydrobromide and nitrate or salts with an organic acid such as maleate, fumarate, malate, tartrate, succinate, citrate, acetate, lactate, methanesulfonate, p-toluenesulfonate or pamoate.

When the compounds of the present invention possess one or more chiral carbon atoms, there exist racemates, diastereoisomers and individual optical isomers thereof, and the present invention embraces all of them.

Preferable compounds of the present invention are the compound (I) wherein Ar is pyridyl, phenyl or substituted phenyl by one to three substituents optionally selected from the group consisting of halogen, hydroxy, straight or branched chain alkyl having 1 to 5 carbon atoms and straight or branched chain alkoxy having 1 to 5 carbon atoms, A is alkylene having 1 to 8 carbon atoms or substituted alkylene having 1 to 8 carbon atoms by straight or branched chain alkyl having 1 to 5 carbon atoms, $R^1$ is hydrogen, $R^2$ and $R^3$ are the same or different and each is hydrogen or straight or branched chain alkyl having 1 to 5 carbon atoms, and $R^4$, $R^5$ and $R^6$ are the same or different and each is hydrogen, hydroxy, straight or branched chain alkyl having 1 to 8 carbon atoms, straight or branched chain alkoxy having 1 to 8 carbon atoms, phenyl, phenoxy, aralkyl, aralkyloxy, or substituted phenyl, phenoxy, aralkyl or aralkyloxy by one to three substituents selected from the group consisting of halogen, straight or branched chain alkyl having 1 to 5 carbon atoms, and straight or branched chain alkoxy having 1 to 5 carbon atoms on the aromatic ring, and pharmaceutically acceptable acid addition salts thereof.

More preferable compounds of the present invention are the compounds selected from the group consisting of 4-(2-chlorophenyl)-2-[2-(4-isobutylphenyl)ethyl]-9-methyl-6H-thieno[3,2-f][1,2,4]triazolo[4,3-a][1,4]diazepine, 4-(2-chlorophenyl)-2-[2-(4-methylphenyl)ethyl]-9-methyl-6H-thieno-[3,2-f][1,2,4]triazolo[4,3-a][1,4]diazepine, 4-(2-chlorophenyl)-2-[4-(4-isobutylphenyl)butyl]-9-methyl-6H-thieno[3,2-f][1,2,4]triazolo[4,3-a][1,4]diazepine, 4-(2-chlorophenyl)-2-[2-(4-methoxyphenyl)ethyl]-9-methyl-6H-thieno[3,2-f][1,2,4]triazolo[4,3-a][1,4]diazepine, 4-(2-chlorophenyl)-2-[2-(4-n-butylphenyl)ethyl]-9-methyl-6H-thieno[3,2-f][1,2,4]triazolo[4,3-a][1,4]diazepine, 4-(2-chlorophenyl)-2-[2-(4-phenylphenyl)ethyl]-9-methyl-6H-thieno[3,2-f][1,2,4]triazolo[4,3-a][1,4]diazepine, 4-(2-chlorophenyl)-2-(2-phenylethyl)-9-methyl-6H-thieno[3,2-f][1,2,4]triazolo[4,3-a][1,4]diazepine, 4-(2-chlorophenyl)-2-(4-isobutylbenzyl)-9-methyl-6H-thieno[3,2-f][1,2,4]triazolo[4,3-a][1,4]diazepine, 4-(2-chlorophenyl)-2-[3,-(4-isobutylphenyl)propyl]-9-methyl-6H-thieno[3,2-f][1,2,4]triazolo[4,3-a][1,4]diazepine, 4-(2-chlorophenyl)-9-ethyl-2-[2-(4-isobutylphenyl)ethyl]-6H-thieno-[3,2-f[1,2,4]triazolo[4,3-a][1,4]diazepine, 4-(2-chlorophenyl)-2-[2-(4-isobutylphenyl)ethyl]-6,9-dimethyl-6H-thieno[3,2-f][1,2,4]triazolo[4,3-a][1,4]diazepine and 4-(2-chlorophenyl)-2-[2-(4-n-butylphenyl)ethyl]-6,9-dimethyl-6H-thieno[3,2-f][1,2,4]triazolo[4,3-a][1,4 ]diazepine.

The compounds of formula (I) of the present invention can be prepared by reacting a compound of the formula:

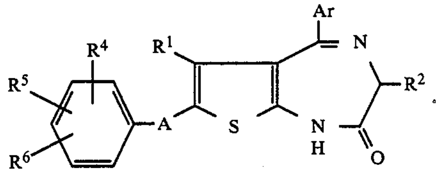

(II)

wherein each symbol is as defined above, with a thionating agent and then reacting thus obtained compound of formula:

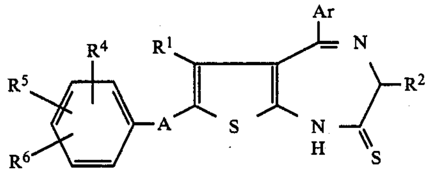

(III)

wherein each symbol is as defined above, with a compound of the formula:

$R^3CONHNH_2$ (IV)

wherein $R^3$ is as defined above. The compounds of formula (I) can also be prepared by the compound of formula (III) with hydrazine hydrate and then reacting the obtained compound of formula:

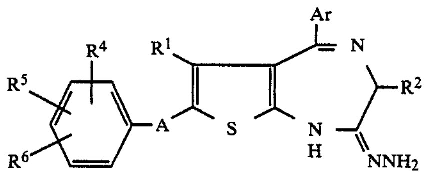

(V)

wherein each symbol is as defined above, with a compound of the formula:

$R^3COOH$ (VI)

wherein $R^3$ is as defined above, or reactive derivatives thereof, or with a compound of the formula:

$R^3C(OR^7)_3$ (VII)

wherein $R^7$ is alkyl having 1 to 5 carbon atoms (e.g. methyl or ethyl) and $R^3$ is as defined above.

In the above reaction, thionating agent includes, for example, phosphorus pentasulfide and Lawesson reagent, i.e. 2,4-bis(4-methoxyphenyl)-1,3,2,4-dithiadiphosphetan-2,4-disulfide, and the reactive derivatives of compound (VI) include, for example, an acid halide, an acid anhydride, a mixed acid anhydride, a $C_{1-5}$ alkyl ester and a benzyl ester.

The reaction of the compound (II) with the thionating agent is usually carried out at 30°-100° C. in an inert solvent (e.g. pyridine, dimethylaniline, benzene, toluene, xylene, tetrahydrofuran, chloroform, dioxane or a mixed solvent thereof) for 30 minutes to 5 hours.

The reaction of the compound (III) with the compound (IV) is usually carried out at a temperature of from room temperature to the refluxing temperature of the employed solvent in an inert solvent (e.g. benzene, toluene, xylene, tetrahydrofuran, dioxane or a mixed solvent thereof) in the presence of an organic acid (e.g. acetic acid or propionic acid), an inorganic acid (e.g. hydrochloric acid or sulfuric acid) or silica gel for 30 minutes to 5 hours.

The reaction of the compound (III) with hydrazine hydrate is usually carried out at 0°-40° C. in an inert solvent (e.g. methanol, ethanol, propanol, isopropyl alcohol or butanol) for 5 minutes to 3 hours.

The reaction of the compound (V) with the compound (VI) or reactive derivative thereof or the compound (VII) is usually carried out at a temperature of from room temperature to the refluxing temperature of the employed solvent in an inert solvent (e.g. benzene, toluene, xylene, tetrahydrofuran, dioxane or a mixed solvent thereof) in the presence of an organic acid (e.g. acetic acid or propionic acid), an inorganic acid (e.g. hydrochloric acid or sulfuric acid) or silica gel for 30 minutes to 6 hours.

The compound of the formula (I) wherein at least one of $R^4$, $R^5$ and $R^6$ is hydroxy or Ar is substituted phenyl by hydroxy can be prepared by dealkylating the compound of formula (I) wherein at least one of $R^4$, $R^5$ and $R^6$ is alkoxy as defined above, or Ar is substituted phenyl by alkoxy.

The dealkylating agent includes, for example, hydrobromic acid-acetic acid, aluminum chloride, methioninemethanesulfonic acid, lower alkyldisulfide-aluminum chloride or the like. The reaction is usually carried out at a temperature of from room temperature to the refluxing temperature of the employed solvent in an inert solvent (e.g. acetic acid, methylene chloride, chloroform, dichloroethane or methanesulfonic acid) for 1 to 24 hours.

The compound of formula (I) wherein at least one of $R^4$, $R^5$ and $R^6$ is alkoxy or aralkyloxy can be prepared by reacting the compound of formula (I) wherein at least one of $R^4$, $R^5$ and $R^6$ is hydroxy, with a compound of formula:

$R^8$—X (VIII)

wherein $R^8$ is alkyl or aralkyl as defined in $R^4$, $R^5$ and $R^6$ and X is halogen (e.g. chlorine or bromine), or methanesulfonyloxy or sulfonyloxy. The reaction is usually carried out at 0° C. to the refluxing temperature of the employed solvent, preferably, in the presence of a base such as an alkali bicarbonate, an alkali carbonate, an alkali hydroxide, sodium hydride, sodium amide or triethylamine in an inert solvent (e.g. ethanol, methanol, dimethylformamide, dioxane or 2-methoxyethanol) for 30 minutes to 24 hours.

The compounds of formula (I) can be isolated and purified from thus obtained resulting mixture by means of a known and conventional manner such as recrystallization or chromatography.

The compounds of formula (I) can be converted into the above-mentioned pharmaceutically acceptable salts by treating the compounds with inorganic or organic acids in a conventional manner.

The compounds of the present invention having the chiral carbon atom can be usually prepared as racemates. The racemates can be divided into optical isomers by a conventional method. Such optical isomers can also be prepared by using optically active starting compounds. The individual diastereoisomer can be purified by means of fractional recrystallization or chromatography.

The compounds of the present invention are exemplified in the following Compound Tables:

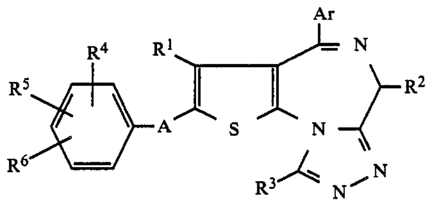
| 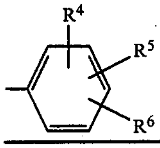 | —A— | Ar | $R^1$ | $R^2$ | $R^3$ | M.p. (°C.) |
|---|---|---|---|---|---|---|
| 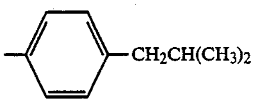 | $-(CH_2)_2-$ | 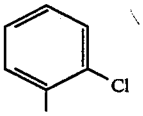 | H | H | $CH_3$ | 118–121 |
| 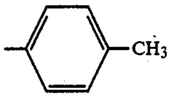 | $-(CH_2)_2-$ | 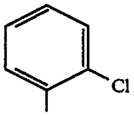 | H | H | $CH_3$ | 160–162 |
| 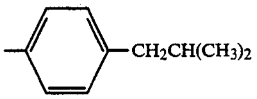 | $-(CH_2)_4-$ | 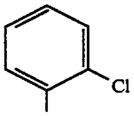 | H | H | $CH_3$ | (oil) |
| 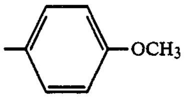 | $-(CH_2)_2-$ | 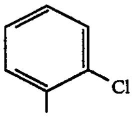 | H | H | $CH_3$ | 100–105 |
| 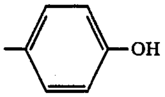 | $-(CH_2)_2-$ | 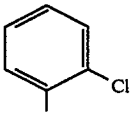 | H | H | $CH_3$ | 100–102 |
| 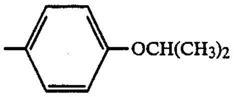 | $-(CH_2)_2-$ | 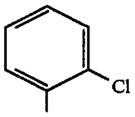 | H | H | $CH_3$ | 121–124 |
| 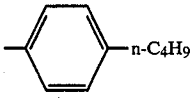 | $-(CH_2)_2-$ | 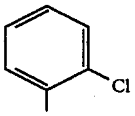 | H | H | $CH_3$ | 119–121 |
| 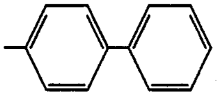 | $-(CH_2)_2-$ | 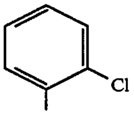 | H | H | $CH_3$ | 163–165 |
| 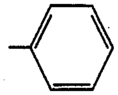 | $-CH_2-$ | 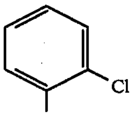 | H | H | $CH_3$ | 161–163 |

-continued
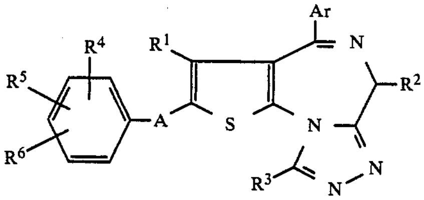
| 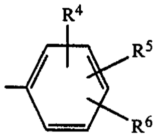 | —A— | Ar | $R^1$ | $R^2$ | $R^3$ | M.p. (°C.) |
|---|---|---|---|---|---|---|
| 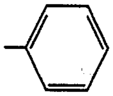 | $—(CH_2)_2—$ | 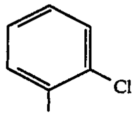 | H | H | $CH_3$ | 106–108 |
| 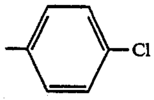 | $—(CH_2)_2—$ | 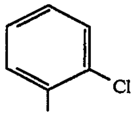 | H | H | $CH_3$ | 162–164 |
| 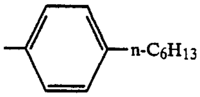 | $—(CH_2)_2—$ | 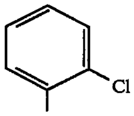 | H | H | $CH_3$ | (oil) |
| 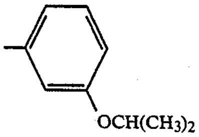 | $—(CH_2)_2—$ | 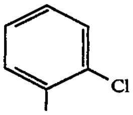 | H | H | $CH_3$ | 105–106 |
| 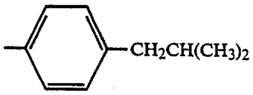 | $—(CH_2)_2—$ | 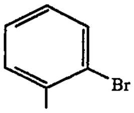 | H | H | $CH_3$ | 153–155 |
| 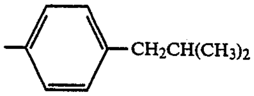 | $—CH_2—$ | 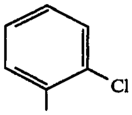 | H | H | $CH_3$ | 134–136 |
| 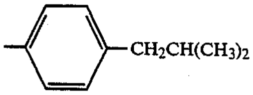 | $—(CH_2)_3—$ | 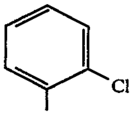 | H | H | $CH_3$ | 122–125 |
| 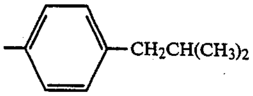 | $—(CH_2)_2—$ | 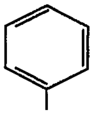 | H | H | $CH_3$ | 121–122 |
| 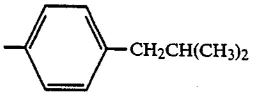 | $—(CH_2)_2—$ | 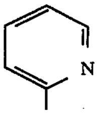 | H | H | $CH_3$ | |

-continued
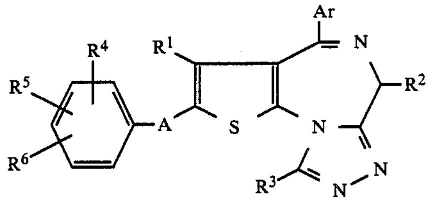
| 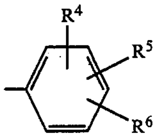 | —A— | Ar | $R^1$ | $R^2$ | $R^3$ | M.p. (°C.) |
|---|---|---|---|---|---|---|
| 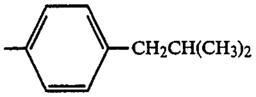 | $-(CH_2)_2-$ | 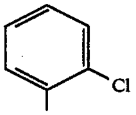 | H | H | $C_2H_5$ | 115–116 |
| 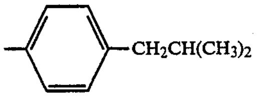 | $-(CH_2)_2-$ | 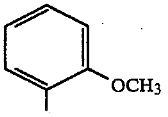 | H | H | $CH_3$ | (oil) |
| 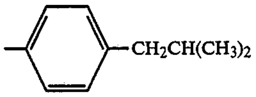 | $-(CH_2)_2-$ | 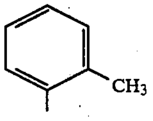 | H | H | $CH_3$ | 105–107 |
| 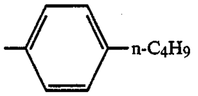 | $-(CH_2)_2-$ | 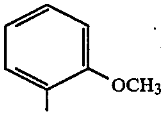 | H | H | $CH_3$ | 109.5–111 |
| 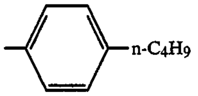 | $-(CH_2)_2-$ | 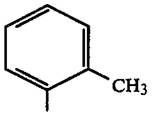 | H | H | $CH_3$ | 91–93 |
| 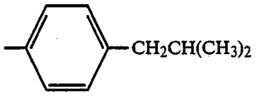 | $-\overset{CH_3}{\overset{\vert}{C}}HCH_2CH_2\overset{CH_3}{\overset{\vert}{C}}H-$ | 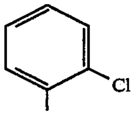 | H | H | $CH_3$ | |
| 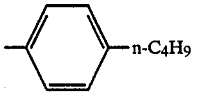 | $-(CH_2)_4-$ | 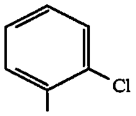 | H | H | $CH_3$ | (oil) |
| 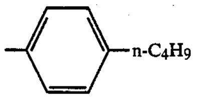 | $-(CH_2)_2-$ | 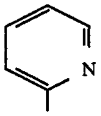 | H | H | $CH_3$ | |
| 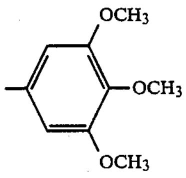 | $-(CH_2)_2-$ | 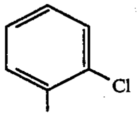 | H | H | $CH_3$ | 166–168 |

-continued
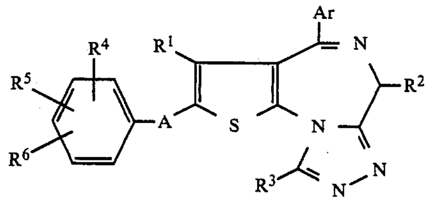
| 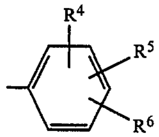 | —A— | Ar | $R^1$ | $R^2$ | $R^3$ | M.p. (°C.) |
|---|---|---|---|---|---|---|
| 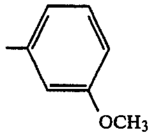 | $-(CH_2)_2-$ | 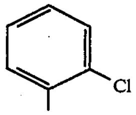 | H | H | $CH_3$ | 100–102 |
| 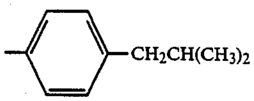 | $-(CH_2)_2-$ | 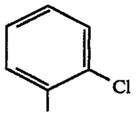 | H | H | $C_3H_7$ | 74–77 |
| 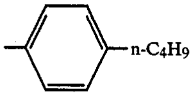 | $-(CH_2)_2-$ | 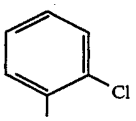 | H | H | $C_2H_5$ | 119–120 |
| 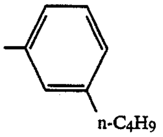 | $-(CH_2)_2-$ | 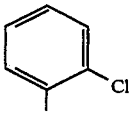 | H | H | $CH_3$ | |
| 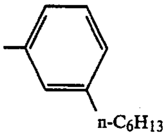 | $-(CH_2)_2-$ | 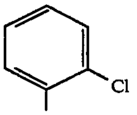 | H | H | $CH_3$ | |
| 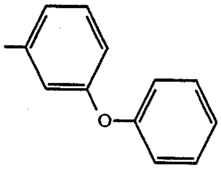 | $-(CH_2)_2-$ | 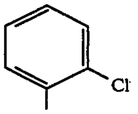 | H | H | $CH_3$ | 131–133 |
| 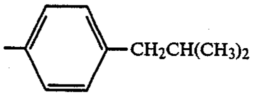 | $-(CH_2)_2-$ | 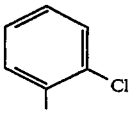 | H | $CH_3$ | $CH_3$ | 129.5–131.5 |
| 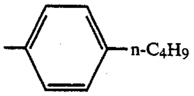 | $-(CH_2)_2-$ | 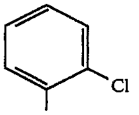 | H | $CH_3$ | $CH_3$ | 105–107 |

-continued
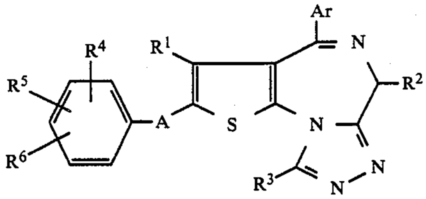
| 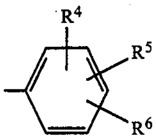 | —A— | Ar | $R^1$ | $R^2$ | $R^3$ | M.p. (°C.) |
|---|---|---|---|---|---|---|
| 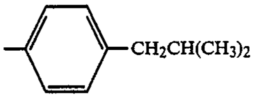 | $-(CH_2)_2-$ | 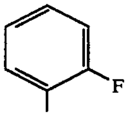 | H | H | $CH_3$ | 122–124 |
| 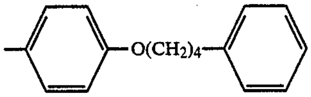 | $-(CH_2)_2-$ | 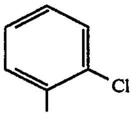 | H | H | $CH_3$ | |
| 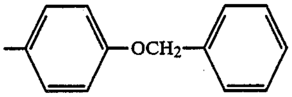 | $-(CH_2)_2-$ | 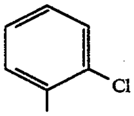 | H | H | $CH_3$ | 126–128 |
| 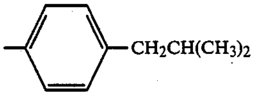 | $-(CH_2)_2-$ | 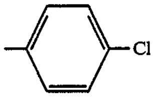 | H | H | $CH_3$ | 165–167 |
| 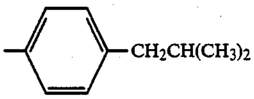 | $-(CH_2)_2-$ | 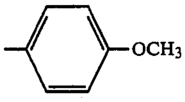 | H | H | $CH_3$ | 124–126 |
| 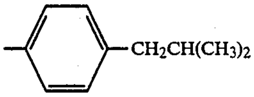 | $-(CH_2)_2-$ | 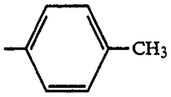 | H | H | $CH_3$ | 140–142 |
| 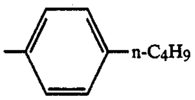 | $-(CH_2)_2-$ | 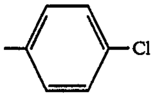 | H | H | $CH_3$ | 135–137 |
| 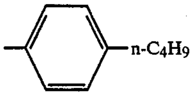 | $-(CH_2)_2-$ | 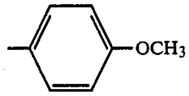 | H | H | $CH_3$ | 110–112 |
| 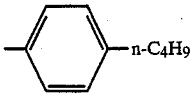 | $-(CH_2)_2-$ | 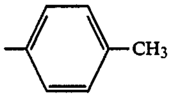 | H | H | $CH_3$ | 112–114 |
| 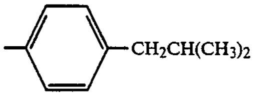 | $-(CH_2)_2-$ | 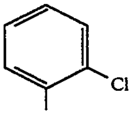 | $CH_3$ | H | $CH_3$ | |

-continued
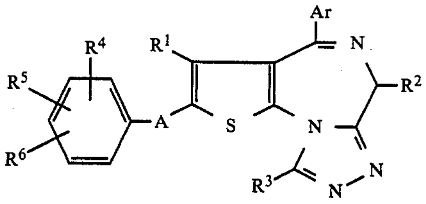
| 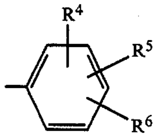 | —A— | Ar | $R^1$ | $R^2$ | $R^3$ | M.p. (°C.) |
|---|---|---|---|---|---|---|
| 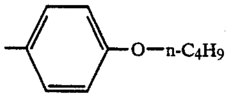 | $-(CH_2)_2-$ | 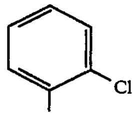 | H | H | $CH_3$ | 137–139 |
| 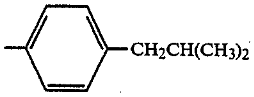 | $-(CH_2)_2-$ | 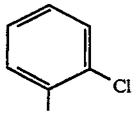 | H | H | H | 98–100 |
| 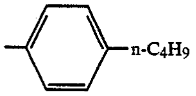 | $-(CH_2)_2-$ | 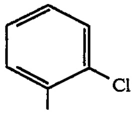 | H | H | H | |
| 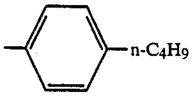 | $-(CH_2)_2-$ | 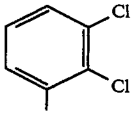 | H | H | $CH_3$ | |
| 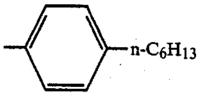 | $-(CH_2)_2-$ | 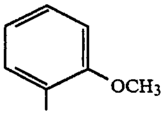 | H | H | $CH_3$ | (oil) |
| 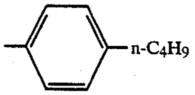 | $-CH_2CH_2\overset{CH_3}{CH}-$ | 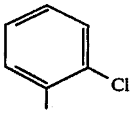 | H | H | $CH_3$ | |
| 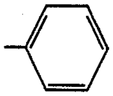 | $-CH_2CH_2\overset{CH_3}{CH}-$ | 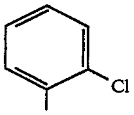 | H | H | $CH_3$ | |
| 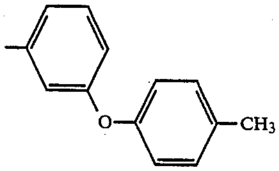 | $-(CH_2)_2-$ | 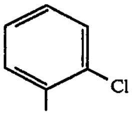 | H | H | $CH_3$ | |
| 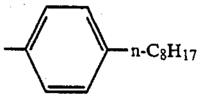 | $-(CH_2)_2-$ | 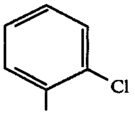 | H | H | $CH_3$ | 112–114 |

-continued
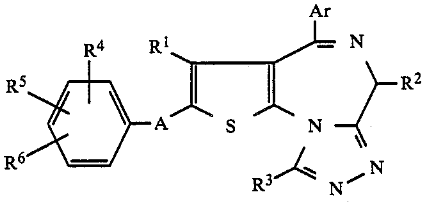
| 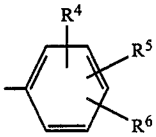 | —A— | Ar | $R^1$ | $R^2$ | $R^3$ | M.p. (°C.) |
|---|---|---|---|---|---|---|
| 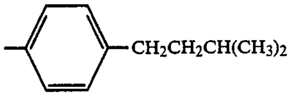 | $-(CH_2)_2-$ | 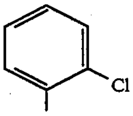 | H | H | $CH_3$ | |
| 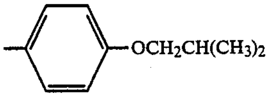 | $-(CH_2)_2-$ | 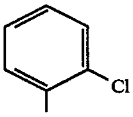 | H | H | $CH_3$ | |
| 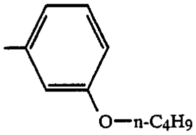 | $-(CH_2)_2-$ | 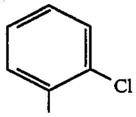 | H | H | $CH_3$ | |
| 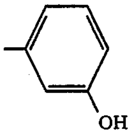 | $-(CH_2)_2-$ | 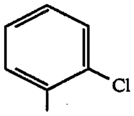 | H | H | $CH_3$ | 215–216 |
| 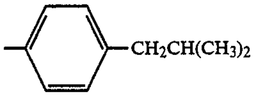 | $-(CH_2)_2-$ | 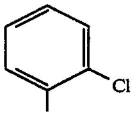 | H | $C_2H_5$ | $CH_3$ | 97–99 |
| 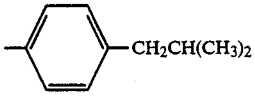 | $-(CH_2)_2-$ | 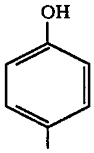 | H | H | $CH_3$ | 240–242 |
| 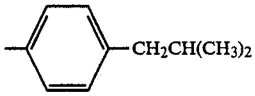 | $-CH_2-$ | 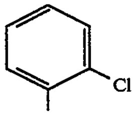 | H | $CH_3$ | $CH_3$ | |
| 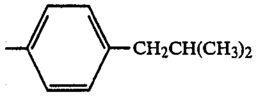 | $-(CH_2)_3-$ | 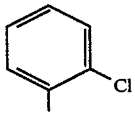 | H | $CH_3$ | $CH_3$ | |

-continued

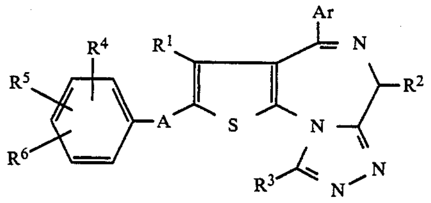

| 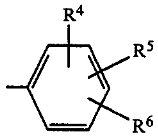 | —A— | Ar | $R^1$ | $R^2$ | $R^3$ | M.p. (°C.) |
|---|---|---|---|---|---|---|
| 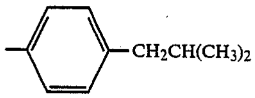 | $-(CH_2)_2-$ | 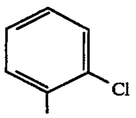 | H | $C_4H_9$ | $CH_3$ | |
| 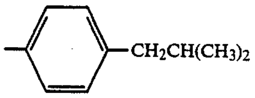 | $-(CH_2)_2-$ | 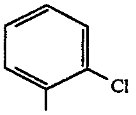 | H | $CF_3$ | $CH_3$ | |
| 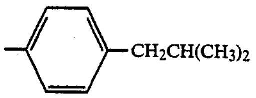 | $-(CH_2)_2-$ | 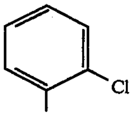 | H | $CH_3$ | $CF_3$ | |
| 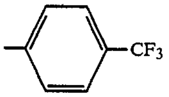 | $-(CH_2)_2-$ | 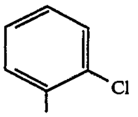 | H | $CH_3$ | $CH_3$ | |
| 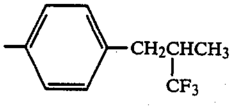 | $-(CH_2)_2-$ | 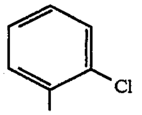 | H | H | $CH_3$ | |

The starting compounds of formula (II) are also novel and can be prepared by reacting a compound of the formula:

$$ArCOCH_2CN \quad (IX)$$

wherein Ar is as defined above, with a compound of the formula:

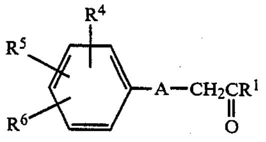

(X)

wherein each symbol is as defined above, in the presence of sulfur at a room temperature or under heating in a solvent such as an alcoholic solvent, dimethylformamide or dimethylacetamide with a base catalyst such as triethylamine, pyrrolidine, piperidine or morpholine, reacting a resulting compound of the formula:

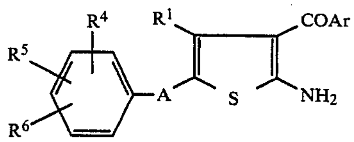

(XI)

wherein each symbol is as defined above, with a compound of the formula:

$$Z^1COCHZ^2 \quad (XII)$$
$$\quad | $$
$$\quad R^2$$

wherein $Z^1$ and $Z^2$ are the same or different and each is halogen such as chlorine or bromine, and $R^2$ is as defined above, and reacting a N-bromo- or chloro-acetyl compound thus obtained, or, if desired, an N-iodoacetyl compound which is prepared by treating the N-bromo- or chloro-acetyl compound with potassium iodide or sodium iodide, with ammonia under cooling or heating in a solvent such as acetone, tetrahydrofuran or dioxane in the course of the above reaction, and then subjecting thus obtained N-glycyl compound to ring closure reaction with dehydration under heating in an inert solvent (e.g. ethanol, propanol, isopropyl alcohol, butanol, benzene, toluene or dimethylformamide), preferably in the presence of a weak acid catalyst such as acetic acid or propionic acid.

In order to determine PAF-antagonistic activity of the compounds of the present invention, the antagonistic effects on PAF-induced platelet aggregation in rabbits (in vitro and ex vivo tests), or inhibitory effects on PAF-induced lethal shock in mice and PAF-induced foot edema in rats were investigated.

The test compounds employed are as follows:

Compound A: 4-(2-chlorophenyl)-2-[2-(4-isobutylphenyl)ethyl]9-methyl-6H-thieno[3,2-f][1,2,4]triazolo[4,3-a][1,4]diazepine Compound B: 4-(2-chlorophenyl)-2-[2-(4-methylphenyl)ethyl]9-methyl-6H-thieno[3,2-f][1,2,4]triazolo[4,3-a][1,4]diazepine Compound C: 4-(2-chlorophenyl)-2-[4-(4-isobutylphenyl)butyl]9-methyl-6H-thieno[3,2-f][1,2,4]triazolo[4,3-a][1,4]diazepine Compound D: 4-(2-chlorophenyl)-2-[2-(4-methoxyphenyl)ethyl]9-methyl-6H-thieno[3,2-f][1,2,4]triazolo[4,3-a][1,4]diazepine Compound E: 4-(2-chlorophenyl)-2-[2-(4-n-butylphenyl)ethyl]9-methyl-6H-thieno[3,2-f][1,2,4triazolo[4,3-a][1,4]diazepine Compound F: 4-(2-chlorophenyl)-2-[2-(4-phenylphenyl)ethyl]9-methyl-6H-thieno[3,2-f][1,2,4]triazolo[4,3-a][1,4]diazepine Compound G: 4-(2-chlorophenyl)-2-(2-phenylethyl)-9-methyl-6H-thieno[3,2-f][1,2,4]trizolo[4,3-a][1,4]diazepine Compound H: 4-(2-chlorophenyl)-2-(4-isobutylbenzyl)-9-methyl-6H-thieno[3,2-f][1,2,4]triazolo[4,3-a][1,4]diazepine Compound I: 4-(2-chlorophenyl)-2-[3-(4-isobutylphenyl)propyl]9-methyl-6H-thieno[3,2-f][1,2,4]triazolo[4,3-a][1,4]diazepine Compound J: 4-(2-chlorophenyl)-9-ethyl-2-[2-(4-isobutylphenyl)ethyl]-6H-thieno[3,2-f][1,2,4]triazolo[4,3-a][1,4]diazepine Compound K: 4-(2-chlorophenyl)-2-[2-(4-isobutylphenyl)ethyl]6,9-dimethyl-6H-thieno[3,2-f][1,2,4]triazolo[4,3-a][1,4]diazepine Compound L: 4-(2-chlorophenyl)-2-[2-(4-n-butylphenyl)ethyl]6,9-dimethyl-6H-thieno[3,2-f][1,2,4]triazolo[4,3-a][1,4]diazepine Experiment 1: Inhibitory effect on platelet aggregation in rabbits (in vitro test)

Blood samples to which was added 0.1 volume of 3.8% sodium citrate were collected from rabbits. Platelet rich plasma (PRP) was prepared by centrifuging the blood sample at 200×g for 10 minutes, and platelet poor plasma (PPP) was prepared by centrifuging the remaining blood sample at 1000×g for 10 minutes.

Aggregation ability was measured with a turbidimetric device (6-channel NKK Hematracer 1, model PAT-6A) according to the method of G.V.R. Born described in J. Physiology, vol. 168, p. 178 (1963). The aggregometer was adjusted in sensitivity to give light transmission vaues of 0 and 100% for PRP and PPP, respectively. With stirring at 1000 rpm, 0.3 μl of test compound solution or vehicle was added to 0.3 ml of PRP. After the mixture was kept at 37° C. for 2 minutes, to the mixture was added 3 μl PAF (Serdary Research Lab.) at the final concentration of $1.8\times10^{-7}$M and the light transmission was recorded for 5 minutes.

In all experiments, PAF was dissolved in ethanol at the concentration of 100 μg/ml, and, when used, diluted with 0.9% saline solution.

The inhibition percentage of test compounds on platelet aggregation were calculated from the following formula by measuring the maximal light transmission in the presence and absence of the test compounds.

$$\%\text{ of inhibition} = \left(1 - \frac{\text{maximal aggregation in the presence of the test compound}}{\text{maximal aggregation in the absence of the test compound}}\right) \times 100$$

$IC_{50}$ (μg/ml, concentration of 50% inhibition) was graphically determined. The results were summarized in Table 1.

TABLE 1

| Compound | Inhibition of PAF-induced platelet aggregation, $IC_{50}$ (μg/ml) |
|---|---|
| A | 0.003-0.01 |
| B | 0.01-0.03 |
| C | 0.03-0.1 |
| D | 0.01-0.03 |
| E | 0.01 |
| F | 0.01-0.03 |
| G | 0.03-0.1 |
| H | 0.003-0.01 |
| I | 0.01 |
| J | 0.01-0.03 |
| K | 0.01-0.03 |
| L | 0.01-0.03 |
| Etizolam | 1.3 |

Experiment 2: Inhibitory effect on platelet aggregation in rabbits (ex vivo test)

Test compound was orally administered to rabbit instead of adding it to PRP as in vitro test of Experiment 1, and then the citrated blood samples (9 volumes of blood+1 volume of 3.8% sodium citrate) were collected with the passage of time. Then, the blood samples were employed to determine the inhibitory effect at 1, 3, 6 and 24 hours after the administration of test compounds, respectively, according to Experiment 1. The results were shown in Table 2.

TABLE 2

| Compound | Dose (mg/kg) p.o. | Number of Animals | % of inhibition 1 hour | 3 hours | 6 hours | 24 hours |
|---|---|---|---|---|---|---|
| A | 3 | 3 | 97±3 | 100±0 | 100±0 | 100±0 |
| E | 3 | 3 | 100±0 | 100±0 | 100±0 | 94±6 |
| Etizolam | 10 | 3 | no effect | | | |

Experiment 3: Effect on PAF-induced lethal shock in mice

The experiment was carried out according to the method of Young et al. described in Prostaglandins, vol. 30, p. 545 (1985). Groups of 9 to 15 male ICR mice (Charles River) weighing 25-30 g were used. 80 μg/kg of PAF (Serdary Research Lab.) solution was intravenously administered in a lateral tail vein 1 hour after the oral administration of test compound (0.1 ml/10 g). All animals were observed for 24 hours after the PAF injection. Results were given as number of survivors/number of employed animals and survival rates (%) in Table 3.

TABLE 3

| Compound | Dose (mg/kg) p.o. | Number of Survivors / Number of Animals | Survival rate (%) |
|---|---|---|---|
| A | 3.0 | 9/9 | 100.0 |
| C | 3.0 | 9/9 | 100.0 |
| E | 1.0 | 7/10 | 70.0 |
| E | 3.0 | 10/10 | 100.0 |
| Control | 0 | 0/15 | 0 |
| Etizolam | 1.0 | 1/11 | 9.1 |
| | 3.0 | 3/11 | 27.3 |
| | 10.0 | 6/11 | 54.5 |

Experiment 4: Effect on PAF edema

The experiment was carried out according to the method of Swingle et al. described in Agents and Actions, vol. 18, p. 359 (1986). Groups of five male Donryu rats weighing about 150 g were used. One hour after the oral administration of test compound (25 ml/kg), 5 μg/0.05 ml of PAF solution was subcutaneously injected to the paw of the right hind leg. The foot volume of the hind leg was measured 1 hour after the injection. The increasing ratios of foot volume before and after PAF injection were calculated. The results were represented as inhibition percentage to the control group and shown in Table 4.

TABLE 4

| Compound | Dose (mg/kg) | Inhibition (%) |
|---|---|---|
| A | 0.3 | 31 |
| | 1 | 51 |
| | 3 | 59 |
| E | 0.1 | 55 |
| | 1 | 78 |
| | 3 | 75 |
| Etizolam | 10 | 38 |
| | 25 | 54 |

The acute toxicity of the compounds of the present invention was studied in 6 male mice. The mice were observed for 5 days after the oral administration of the compound. All mice survived at the dose of 1000 mg/kg of the compounds.

It becomes clear from the results of the various pharmacological experiments inclusive of those mentioned above that the compounds of the present invention exhibit potent and long-lasting PAF-antagonistic activity, and that such superior activity is also observed by the oral administration of the compounds of the present invention, and further, the PAF-antagonistic activity of the compounds of the present invention is far more potent than that of Etizolam.

Moreover, the compounds of the present invention have less affinity for the benzodiazepine receptor than Etizolam, which is well-known to have high affinity for the receptor, and exhibit no depressive effects on the central system such as sedative or muscle relaxation activity.

In view of the above facts, the compounds of the present invention are useful as PAF-antagonists, and are preventable or treatable various kinds of PAF-induced diseases such as inflammatory diseases, allergic diseases, anaphylactic shocks, septic shocks, myocardiac diseases, asthma, pulmonary edema or adult respiratory diseases.

The compounds of the present invention and pharmaceutically acceptable acid addition salts thereof can be safely administered orally or parenterally in human beings in the form of a pharmaceutical composition such as tablets, pills, powder, capsules, granules, solutions, inhalants, suppositories, percutaneous absorption preparations or injectable solutions. The pharmaceutical composition can be prepared by, for example, mixing a therapeutically effective amount of at least one compound with a pharmaceutically acceptable additives such as an excipient, an extender, a diluent or a solubilizer.

The dose may vary depending upon the compound selected or employed, the severity of the patients to be treated or the age of the patients, but the daily dose for human adults preferably ranges from 0.1 to 100 mg in single or multiple dose.

The starting compounds are novel and can be obtained according to the method described in Journal of Medicinal Chemistry, vol. 16, p. 214 (1973). The followings are illustrated the preparations of such starting compounds in detail.

EXAMPLES FOR STARTING COMPOUND (a)

2-amino-3-(2-chlorobenzoyl)-5-[2-(4-isobutylphenyl)ethyl]thiophene

To a suspension of 29 g of 2-chlorocyanoacetophenone and 4.9 g of sulfur in 50 ml of dimethylformamide is added 18.5 g of triethylamine with stirring. To the mixture is, then, added a solution of 30 g of 4-(4-isobutylphenyl)butylaldehyde in 10 ml of ethanol and stirred at 60° C. for 3 hours. The resultant mixture is poured into ice-cold water and extracted with 400 ml of chloroform. The extract is washed with water and dried over anhydrous magnesium sulfate. After filtering off, the filtrate is concentrated under reduced pressure to give 70 g of the above-mentioned amino compound as oil.

(b)

2-chloroacetylamino-3-(2-chlorobenzoyl)-5-[2-(4-isobutylphenyl)ethyl]-thiophene

To a solution of 70 g of the compound (a) in 500 ml of chloroform is added 20 g of chloroacetyl chloride and the mixture is refluxed under heating with stirring for 2 hours. After cooling, the mixture is washed with an aqueous sodium hydrogencarbonate solution and sodium chloride solution, and dried over anhydrous magnesium sulfate. After filtering off, the filtrate is concentrated under reduced pressure. The residue is subjected to chromatography on silica gel to give 45 g of the above-mentioned chloroacetylamino compound as crude oil.

(c)

2-aminoacetylamino-3-(2-chlorobenzoyl)-5-[2-(4-isobutylphenyl)ethyl]-thiophene

A suspension of 45 g of the chloroacetylamino compound (b) and 16 g of sodium iodide in 200 ml of tetrahydrofuran is refluxed under heating with stirring for 2 hours. After standing to cool, the mixture is cooled to −20° C. with dry ice-methanol and about 30 ml of liquid ammonia with stirring is added thereto. The temperature of the resulting solution is gradually raised to room temperature over 2 hours. After the ammonia is removed with an aspirator, the mixture is concentrated under reduced pressure and the residue is dissolved in 500 ml of chloroform. The solution is washed with water and dried over anhydrous magnesium sulfate. After filtering off, the filtrate is concentrated under reduced pressure to give 50 g of the titled amino compound as crude oil.

(d)
5-(2-chlorophenyl)-7-[2-(4-isobutylphenyl)ethyl-]1,3-dihydro-2H-thieno[2,3-e]-1,4-diazepin-2-one To a solution of 50 g of the above compound (c) in 300 ml of isopropyl alcohol is added 8.5 g of acetic acid and the mixture is refluxed under heating with stirring for 6 hours. The mixture is concentrated under reduced pressure and the residue is dissolved in 500 ml of chloroform. The solution is washed with an aqueous sodium hydrogencarbonate solution and sodium chloride solution and dried over anhydrous magnesium sulfate. After filtering off, the filtrate is concentrated under reduced pressure. The residue is subjected to chromatography on silica gel and eluted with a chloroform-methanol (100:1 to 100:3) solvent. The eluate of the objective fraction is concentrated under reduced pressure and the residue is crystallized from isopropyl ether to give 10 g of the above-mentioned thienodiazepine compound as colorless crystals, melting at 179°-181° C.

The present invention will be explained by the following examples in more detail, but these examples are not to be construed as limiting the present invention.

EXAMPLE 1

4-(2-chlorophenyl)-2-[2-(4-isobutylphenyl)ethyl]-9-methyl-6H-thieno[3,2-f][1,2,4]triazolo[4,3-a][1,4]diazepine A suspension of 9.8 g of 5-(2-chlorophenyl)-7-[2-(4-isobutylphenyl)ethyl]-1,3-dihydro-2H-thieno[2,3-e]-1,4-diazepin-2-one and 5.5 g of Lawesson reagent in 200 ml of toluene is stirred at 40°-43° C. for an hour. The resultant solution is concentrated under reduced pressure, and the residue is subjected to chromatography on silica gel and then eluted with chloroformmethanol (100:1 to 100:2). The objective fraction is concentrated under reduced pressure to give 9.6 g of 5-(2-chlorophenyl)-7-[2-(4-isobutylphenyl)ethyl]-1,3-dihydro-2H-thieno[2,3-e]-1,4-diazepine-2-thione, melting at 180°-182° C. with decomposition.

To a suspension of 9.6 g of 5-(2-chlorophenyl)-7-[2-(4-isobutylphenyl)ethyl]-1,3-dihydro-2H-thieno[2,3-e]-1,4-diazepine-2-thione in 100 ml of methanol is added 3.5 g of 100% hydrazine hydrate under ice-cooling and the mixture is stirred for 30 minutes. After the methanol is fully distilled off at 30°-40° C., to the residue is added 100 ml of chloroform. The solution is dried over anhydrous magnesium sulfate, separated by filtration. The filtrate is concentrated under reduced pressure to give 8 g of 5-(2-chlorophenyl)-7-[2-(4-isobutylphenyl)ethyl]-1,3-dihydro-2H-thieno[2,3-e]-1,4-diazepine-2-hydrazone as oil.

To a solution of the oil in 100 ml of toluene is added 5 g of acetic acid anhydride with stirring under ice-cooling and the mixture is stirred for about 30 minutes. To the resulting mixture is added 6 g of acetic acid, and the mixture is refluxed under heating with stirring for 1 hour, then concentrated under reduced pressure. A solution of the residue in chloroform is washed with sodium hydrogen-carbonate solution and sodium chloride solution and dried over anhydrous magnesium sulfate. After separating by the filtration, the filtrate is concentrated under reduced pressure. The obtained residue is subjected to chromatography on silica gel and eluted with a chloroformmethanol (100:1 to 100:3) solvent. The eluate of the objective fraction is concentrated under reduced pressure and the residue is crystallized from ethyl acetate to give 4.2 g of 4-(2-chlorophenyl)-2-[2-(4-isobutylphenyl)ethyl]-9-methyl-6H-thieno[3,2-f][1,2,4]triazolo][4,3-a][1,4]diazepine as colorless crystals, melting at 118°-121° C.

The above compound can be obtained by reacting the thione compound with acetic acid hydrazide instead of hydrazine hydrate in a similar manner.

EXAMPLE 2

4-(2-chlorophenyl)-2-[2-(4-methylphenyl)ethyl]-9-methyl-6H-thieno[3,2-f][1,2,4]triazolo[4,3-a][1,4]diazepine A suspension of 3.9 g of 5-(2-chlorophenyl)-7-[2-(4-methylphenyl)ethyl]-1,3-dihydro-2H-thieno[2,3-e]-1,4-diazepin-2-one, melting at 195°-197° C. and 2.5 g of Lawesson reagent in 50 ml of toluene is stirred at 40°-43° C. for an hour. The resultant solution is concentrated under reduced pressure, and the residue is subjected to chromatography on silica gel and then eluted with chloroform-methanol (100:1 to 100:2). The objective fraction is concentrated under reduced pressure to give 4 g of 5-(2-chlorophenyl)-7-[2-(4-methylphenyl)ethyl]-1,3-dihydro-2H-thieno[2,3-e]-1,4-diazepine-2-thione, melting at 190°-191° C. with decomposition.

To a suspension of 5 g of 5-(2-chlorophenyl)-7-[2-(4-methylphenyl)ethyl]-1,3-dihydro-2H-thieno[2,3-e]-1,4-diazepine-2-thione in 50 ml of methanol is added 2 g of 100% hydrazine hydrate under ice-cooling and the mixture is stirred for 30 minutes. After the methanol is fully distilled off at 30°-40° C., to the residue is added 100 ml of chloroform and the solution is dried over anhydrous magnesium sulfate. After separating by filtration, the filtrate is concentrated under reduced pressure and the residue is dissolved in 100 ml of toluene. To the solution is added 3 g of acetic anhydride with stirring under ice-cooling and the mixture is stirred for 30 minutes. Then, to the resulting mixture is added 4.4 g of acetic acid and refluxed under heating with stirring for 1 hour. After the reaction mixture is concentrated under reduced pressure, a solution of the residue in chloroform is washed with an aqueous sodium hydrogencarbonate solution and sodium chloride solution, and dried over anhydrous magnesium sulfate. After separating by filtration, the filtrate is concentrated under reduced pressure, the residue is subjected to chromatography on silica gel and eluted with a chloroformmethanol (100:1 to 100:3) solvent. The eluate of the objective fraction is concentrated under reduced pressure and the residue is crystallized from ethyl acetate to give 0.7 g of 4-(2-chlorophenyl)-2-[2-(4-methylphenyl)ethyl]-9-methyl-6H-thieno [3,2-f][1,2,4]triazolo[4,3-a][1,4]diazepine as colorless crystals, melting at 160°-162° C.

EXAMPLE 3

4-(2-chlorophenyl)-2-[4-(4-isobutylphenyl)butyl]-9-methyl-6H-thieno[3,2-f][1,2,4]triazolo[4,3-a][1,4]diazepine A suspension of 8.9 g of 5-(2-chlorophenyl)-7-[4-(4-isobutylphenyl)butyl]-1,3-dihydro-2H-thieno[2,3-e]-1,4-diazepin-2-one, melting at 133°-135° C. and 4.7 g of Lawesson reagent in 100 ml of toluene is stirred at 38°-40° C. for an hour. The resultant solution is concentrated under reduced pressure, and the residue is subjected to chromatography on silica gel and then eluted with chloroform-methanol (100:1 to 100:2). The objective fraction is concentrated under reduced pressure to give 8 g of 5-(2-chlorophenyl)-7-[4-(4-isobutylphenyl)-butyl]-1,3-dihydro-2H-thieno[2,3-e]-1,4-diazepine-2-thione, melting at 169°–171° C. with decomposition.

To a suspension of 8 g of 5-(2-chlorophenyl)-7-[4-(4-isobutylphenyl)butyl]-1,3-dihydro-2H-thieno[2,3-e]-1,4-diazepine-2-thione in 100 ml of methanol is added 2.8 g of 100% hydrazine hydrate with stirring under ice-cooling. The mixture is stirred for 30 minutes and concentrated under reduced pressure. The residue is dissolved in 100 ml of chloroform and dried over anhydrous magnesium sulfate. After separating by filtration, the filtrate is concentrated under reduced pressure to give 8 g of hydrazono-form as oil. To a solution of the hydrazono-form in 100 ml of toluene is added 4 g of acetic anhydride with stirring and stirred for 30 minutes. To the resultant mixture is added 6 g of acetic acid and refluxed under heating for an hour and then concentrated under reduced pressure. A solution of the residue in 100 ml of chloroform is washed with an aqueous sodium hydrogencarbonate solution and sodium chloride solution and dried over anhydrous magnesium sulfate. After separating by filtration, the filtrate is concentrated under reduced pressure. The residue is subjected to chromatography on silica gel and eluted with a chloroform-methanol (100:1 to 100:3) solvent. The eluate of the objective fraction is concentrated under reduced pressure to give 3.8 g of 4-(2-chlorophenyl)-2-[4-(4-isobutylphenyl)butyl]-9-methyl-6H-thieno[3,2-f][1,2,4]trizolo[4,3-a][1,4]diazepine as oil.

EXAMPLE 4

4-(2-chlorophenyl)-2-[2-(4-methoxyphenyl)ethyl]-9-methyl-6H-thieno[3,2-f][1,2,4]triazolo[4,3-a][1,4]diazepine A suspension of 7 g of 5-(2-chlorophenyl)-7-[2-(4-methoxyphenyl)ethyl]-1,3-dihydro-2H-thieno[2,3-e]-1,4-diazepin-2-one, melting at 196°–198° C. and 5 g of Lawesson reagent in 100 ml of toluene is stirred at 45°–48° C. for an hour. The resultant solution is concentrated under reduced pressure, and the residue is subjected to chromatography on silica gel and then eluted with chloroform-methanol (100:1 to 100:2). The objective fraction is concentrated under reduced pressure to give 7 g of 5-(2-chlorophenyl)-7-[2-(4-methoxyphenyl-)ethyl]-1,3-dihydro-2H-thieno[2,3-e]-1,4-diazepine-2-thione, melting at 185°–186° C. with decomposition.

To a suspension of 7 g of 5-(2-chlorophenyl)-7-[2-(4-methoxyphenyl)-ethyl]-1,3-dihydro-2H-thieno[2,3-e]-1,4-diazepine-2-thione in 100 ml of methanol is added 2.7 g of 100% hydrazine and stirred for 30 minutes. The resulting mixture is concentrated at 30°–40° C. and the residue is dissolved in 100 ml of chloroform. After the solution is dried over anhydrous magnesium sulfate, the organic layer is evaporated to dryness and the residue is dissolved in 100 ml of toluene. To the solution is added 5 g of acetic anhydride and the mixture is stirred at the room temperature for about 30 minutes. Moreover, to the reaction solution is added 2.9 g of acetic acid, and refluxed under heating with stirring for an hour and concentrated to dryness. To the residue are added chloroform and water, and neutralized with sodium hydrogencarbonate. The chloroform layer is washed with an aqueous sodium chloride solution, dried over anhydrous magnesium sulfate. After separating by filtration, the filtrate is concentrated and the residue is subjected to chromatography on silica gel and eluted with a chloroform-methanol (100:1 to 100:3) solvent. The eluate of the objective fraction is concentrated and the residue is crystallized from hexane-ethyl acetate to give 4 g of 4-(2-chlorophenyl)-2-[2-(4-methoxyphenyl)ethyl]-9-methyl-6H-thieno[3,2-f][1,2,4]triazolo[4,3-a][1,4]diazepine as colorless crystals, melting at 100°–105° C.

EXAMPLE 5

4-(2-chlorophenyl)-2-[2-(4-hydroxyphenyl)ethyl]-9-methyl-6H-thieno[3,2-f][1,2,4]triazolo[4,3-a][1,4]diazepine A mixture of 1.5 g of thienotriazolodiazepine compound obtained in Example 4 and 5 g of DL-methionine in 100 ml of methanesulfonic acid is allowed to stand at room temperature for 24 hours. The mixture is poured into 300 ml of ice-water, neutrarized with an aqueous sodium hydrogencarbonate solution and extracted with ethyl acetate. The organic layer is washed with a saturated sodium chloride solution and dried over anhydrous magnesium sulfate. After separating by filtration, the filtrate is concentrated to precipitate colorless crystals. The crystals are collected by filtration, washed with isopropyl ether and dried to give 0.9 g of 4-(2-chlorophenyl)-2-[2-(4-hydroxyphenyl)ethyl]-9-methyl-6H-thieno[3,2-f][1,2,4]triazolo[4,3-a][1,4]diazepine, melting at 100°–100° C.

EXAMPLE 6

4-(2-chlorophenyl)-2-[2-(4-isopropoxyphenyl)ethyl]-9-methyl-6H-thieno[3,2-f][1,2,4]triazolo[4,3-a][1,4]diazepine A mixture of 0.5 g of thienotriazolodiazepine compound obtained in Example 5, 0.2 g of potassium hydroxide and 0.62 g of isopropyl iodide in 20 ml of 2-methoxyethanol is stirred at 90° C. for 4 hours, and then the resulting mixture is concentrated to dryness. The residue is dissolved in 50 ml of chloroform, washed with water and dried over anhydrous magnesium sulfate. After separating by filtration, the filtrate is concentrated under reduced pressure and the residue is crystallized from isopropyl ether-ethyl acetate to give 0.3 g of 4-(2-chlorophenyl)-2-[2-(4-isopropoxyphenyl)ethyl]-9-methyl-6H-thieno[3,2-f][1,2,4]triazolo[4,3-a][1,4]diazepine as colorless crystals, melting at 121°–124° C.

EXAMPLE 7

4-(2-chlorophenyl)-2-[2-(4-n-butylphenyl)ethyl]-9-methyl-6H-thieno[3,2-f][1,2,4]triazolo[4,3-a][1,4]diazepine A suspension of 5 g of 5-(2-chlorophenyl)-7-[2-(4-n-butylphenyl)ethyl]-1,3-dihydro-2H-thieno[2,3-e]-1,4-diazepin-2-one, melting at 152°–154° C. and 2.8 g of Lawesson reagent in 100 ml of toluene is stirred at 40°–45° C. for an hour. The resultant solution is concentrated under reduced pressure, and the residue is subjected to chromatography on silica gel and then eluted with chloroform-methanol (100:1 to 100:2). The objective fraction is concentrated under reduced pressure to give 3.8 g of 5-(2-chlorophenyl)-7-[2-(4-n-butylphenyl-)ethyl]-1,3-dihydro-2H-thieno[2,3-e]-1,4-diazepine-2-thione, melting at 186°–188° C. with decomposition.

To a suspension of 3.8 g of 5-(2-chlorophenyl)-7-[2-(4-n-butylphenyl)ethyl]-1,3-dihydro-2H-thieno[2,3-e]-1,4-diazepine-2-thione in 50 ml of methanol is added 1.4 g of 100% hydrazine hydrate and stirred under ice-cooling for 30 minutes. The resultant mixture is concentrated to dryness at 30°-40° C. The residue is dissolved in 100 ml of chloroform and dried over anhydrous magnesium sulfate. After separating by filtration, the chloroform is distilled off and the residue is dissolved in 75 ml of dry toluene. To the solution is added 2.1 g of acetic anhydride and stirred for 30 minutes. Further to the resulting mixture is added 3 g of acetic acid and refluxed under heating with stirring for 2 hours. After standing to cool, the mixture is concentrated to dryness. The residue is dissolved in 100 ml of chloroform and neutrarized with an aqueous sodium hydrogencarbonate solution. The chloroform layer is washed with an aqueous sodium chloride solution, dried over anhydrous magnesium sulfate. After separating by filtration, the filtrate is concentrated. The residue is subjected to chromatography on silica gel and eluted with a chloroform-methanol (100:1 to 100:3) solvent. The eluate of the objective fraction is concentrated and the residue is crystallized from ethyl acetate to give 1 g of 4-(2-chlorophenyl)-2-[2-(4-n-butylphenyl)ethyl]-9-methyl-6H-thieno[3,2-f][1,2,4]triazolo[4,3-a][1,4]diazepine as colorless crystals, melting at 119°-121° C.

EXAMPLE 8

4-(2-chlorophenyl)-2-[2-(4-phenylphenyl)ethyl]-9-methyl-6H-thieno[3,2-f][1,2,4]triazolo[4,3-a][1,4]diazepine A suspension of 7.2 g of 5-(2-chlorophenyl)-7-[2-(4-phenylphenyl)ethyl]-1,3-dihydro-2H-thieno[2,3-e]-1,4-diazepin-2-one, melting at 187°-189° C. and 3.9 g of Lawesson reagent in 100 ml of toluene is stirred at 58°-60° C. for an hour. The resultant solution is concentrated under reduced pressure, and the residue is subjected to chromatography on silica gel and then eluted with chloroform-methanol (100:1 to 100:2). The objective fraction is concentrated under reduced pressure to give 6 g of 5-(2-chlorophenyl)-7-[2-(4-phenylphenyl)ethyl]-1,3-dihydro-2H-thieno[2,3-e]-1,4-diazepine-2-thione, melting at 190°-191° C. with decomposition.

To a suspension of 6 g of 5-(2-chlorophenyl)-7-[2-(4-phenylphenyl)ethyl]-1,3-dihydro-2H-thieno[2,3-e]-1,4-diazepine-2-thione in 100 ml of methanol is added 2.1 g of 100% hydrazine hydrate under ice-cooling and stirred for an hour. The precipitated crystals are collected by filtration and dried to give 5.4 g of hydrazono compound. To a suspension of the compound in 75 ml of toluene is added 1.4 g of acetic anhydride, and stirred for an hour. To the resultant solution is added 4.2 g of acetic acid and refluxed under heating and stirring with removing water for an hour. After cooling, the mixture is concentrated to dryness and the residue is dissolved in 100 ml of chloroform. To the solution is added water, and neutralized with sodium hydrogencarbonate, washed with water and then dried. After separating by filtration, the filtrate is concentrated and the residue is subjected to chromatography on silica gel and eluted with a chloroform-methanol (100:1 to 100:3) solvent. The eluate of the objective fraction is concentrated and the residue is crystallized from ethyl acetate to give 2.8 g of 4-(2-chlorophenyl)-2-[2-(4-phenylphenyl)ethyl]-9-methyl-6H-thieno[3,2-f][1,2,4]triazolo[4,3-a][1,4]diazepine as colorless crystals, melting at 163°-165° C.

EXAMPLE 9

4-(2-chlorophenyl)-2-benzyl-9-methyl-6H-thieno[3,2-f][1,2,4]triazolo[4,3-a][1,4]diazepine A suspension of 5-(2-chlorophenyl)-7-benzyl-1,3-dihydro-2H-thieno[2,3-e]-1,4-diazepin-2-one and 1.2 g of phosphorus pentasulfide in 50 ml of pyridine is stirred at 82° C. for 3 hours. The resultant solution with stirring is poured into ice-cold water. The precipitated crystals are collected by filtration, washed with water and then dried to given 4 g of 5-(2-chlorophenyl)-7-benzyl-1,3-dihydro-2H-thieno[2,3-e]-1,4-diazepine-2-thione, melting at 188°-189° C. with decomposition.

To a suspension of 14 g of 5-(2-chlorophenyl)-7-benzyl-1,3-dihydro-2H-thieno[2,3-e]-1,4-diazepine-2-thione in 50 ml of methanol is added 1.8 g of 100% hydrazine hydrate under ice-cooling and stirred at room temperature for 30 minutes. The methanol is distilled off and the residue is dissolved in 100 ml of chloroform. The solution is washed with a saturated sodium chloride solution and dried over anhydrous magnesium sulfate. After separating by filtration, the filtrate is concentrated to dryness and the residue is dissolved in 50 ml of toluene. To the solution are added 1.3 g of acetic anhydride and 3.8 g of acetic acid, and the mixture is refluxed under heating with stirring for 4.5 hours. The mixture is concentrated to dryness and the residue is dissolved in chloroform. The solution is neutralized with sodium hydrogencarbonate, washed with water and dried over anhydrous magnesium sulfate. After separating by filtration, the filtrate is concentrated, and then the residue is subjected to chromatography on silica gel and eluted with a chloroform-methanol (100:1 to 100:3) solvent. The eluate of the objective fraction is concentrated to dryness and the residue is crystallized from isopropyl ether-ethyl acetate to give 1.5 g of 4-(2-chlorophenyl)-2-benzyl-9-methyl-6H-thieno[3,2-f][1,2,4]triazolo[4,3-a][1,4]diazepine as pale yellow crystals, melting at 161°-163° C.

EXAMPLE 10

4-(2-chlorophenyl)-2-(2-phenylethyl)-9-methyl-6H-thieno[3,2-f][1,2,4]triazolo[4,3-a][1,4]diazepine A suspension of 7.5 g of 5-(2-chlorophenyl)-7-(2-phenylethyl)-1,3-dihydro-2H-thieno[2,3-e]-1,4-diazepin-2-one, melting at 175°-176° C. and 4.8 g of Lawesson reagent in 150 ml of toluene is stirred at 40°-45° C. for an hour. The resultant solution is concentrated under reduced pressure, and the residue is subjected to chromatography on silica gel and then eluted with chloroform-methanol (100:1 to 100:2). The objective fraction is concentrated under reduced pressure to give 9.8 g of 5-(2-chlorophenyl)-7-(2-phenylethyl)-1,3-dihydro-2H-thieno[2,3-e]-1,4-diazepine-2-thione.

To a suspension of 9.8 g of 5-(2-chlorophenyl)-7-(2-phenylethyl)-1,3-dihydro-2H-thieno[2,3-e]-1,4-diazepine-2-thione in 40 ml of methanol is added 3.3 g of 100% hydrazine hydrate with stirring at room temperature and stirred at room temperature for 30 minutes. After the mixture is concentrated under reduced pressure, the resulting oil is dissolved in 20 ml of chloroform, and dried over anhydrous magnesium sulfate and filtered off. The solution is furthermore concentrated under reduced pressure to give 13 g of oil. To a suspension of the oily hydrazono-form in 80 ml of toluene are added 6.4 ml of acetic anhydride and 6.9 ml of acetic acid. The mixture is refluxed under heating with stirring for 45 minutes, and then concentrated under reduced pressure. A solution of the residue in 100 ml of ethyl acetate is washed with an aqueous sodium hydrogencarbonate solution and sodium chloride solution, dried over anhydrous magnesium sulfate and concentrated under reduced pressure. The resulting 6.5 g of oil is subjected to chromatography on silica gel and eluted with a chloroform-methanol (100:1 to 100:3). The eluate of the objective fraction is concentrated under reduced pressure and the residue is crystallized from isopropyl ether-ethyl acetate to give 2 g of 4-(2-chlorophenyl)-2-(2-phenylethyl)-9-methyl-6H-thieno[3,2-f][1,2,4]triazolo[4,3-a][1,4]diazepine as colorless crystals, melting at 106°-108° C.

EXAMPLE 11

4-(2-chlorophenyl)-2-[2-(4-chlorophenyl)ethyl]-9-methyl-6H-thieno[3,2-f][1,2,4]triazolo[4,3-a][1,4]diazepine A suspension of 8.2 g of 5-(2-chlorophenyl)-7-[2-(4-chlorophenyl)ethyl]-1,3-dihydro-2H-thieno[2,3-e]-1,4-diazepin-2-one, melting at 201°-203° C. and 4.9 g of Lawesson reagent in 160 ml of toluene is stirred at 40°-45° C. for an hour. The resultant solution is concentrated under reduced pressure, and the residue is subjected to chromatography on silica gel and then eluted with chloroform-methanol (100:1 to 100:2). The objective fraction is concentrated under reduced pressure to give 4.5 g of 5-(2-chlorophenyl)-7-[2-(4-chlorophenyl)ethyl]-1,3-dihydro-2H-thieno[2,3-e]-1,4-diazepine-2-thione.

To a suspension of 4.5 g of 5-(2-chlorophenyl)-7-[2-(4-chlorophenyl)ethyl]-1,3-dihydro-2H-thieno[2,3-e]-1,4-diazepine-2-thione in 20 ml of methanol is added 1.7 g of 100% hydrazine hydrate under ice-cooling with stirring and the mixture is stirred at room temperature for 15 minutes. After the mixture is concentrated under reduced pressure, the residue is dissolved in 50 ml of chloroform and dried over anhydrous magnesium sulfate, and then concentrated under reduced pressure to give 5.1 g of oil. To a suspension of the oily hydrazonoform in 40 ml of toluene are added 3.4 ml of acetic anhydride and 3.7 ml of acetic acid. The mixture is refluxed under heating with stirring for 45 minutes and concentrated under reduced pressure. The residue is dissolved in 50 ml of ethyl acetate, washed with an aqueous sodium hydrogencarbonate solution and sodium chloride solution, dried over anhydrous magnesium sulfate and then concentrated under reduced pressure to give 3.6 g of oil. The oil is crystallized from isopropyl ether-ethyl acetate. The precipitated crystals are collected by filtration and recrystallized from isopropyl ether-ethyl acetate to give 1.3 g of 4-(2-chlorophenyl)-2-[2-(4-chlorophenyl)ethyl]-9-methyl-6H-thieno[3,2-f][1,2,4]triazolo[4,3-a][1,4]diazepine as colorless crystals, melting at 162°-164° C.

EXAMPLE 12

4-(2-chlorophenyl)-2-[2-(4-n-hexylphenyl)ethyl]-9-methyl-6H-thieno[3,2-f][1,2,4]triazolo[4,3-a][1,4]diazepine A suspension of 6 g of 5-(2-chlorophenyl)-7-[2-(4-n-hexylphenyl)ethyl]-1,3-dihydro-2H-thieno[2,3-e]-1,4-diazepin-2-one, melting at 149°-151° C. and 5.2 g of Lawesson reagent in 100 ml of toluene is stirred at 40°-42° C. for an hour. The resultant solution is concentrated under reduced pressure, and the residue is subjected to chromatography on silica gel and then eluted with chloroform-methanol (100:1 to 100:2). The objective fraction is concentrated under reduced pressure to give 6 g of 5-(2-chlorophenyl)-7-[2-(4-n-hexylphenyl)ethyl]-1,3-dihydro-2H-thieno[2,3-e]-1,4-diazepine-2-thione, melting at 140°-145° C. with decomposition.

To a suspension of 6 g of 5-(2-chlorophenyl)-7-[2-(4-n-hexylphenyl)ethyl]-1,3-dihydro-2H-thieno[2,3-e]-1,4-diazepine-2-thione in 50 ml of methanol is added 2 g of 100% hydrazine hydrate with stirring under ice-cooing and stirred for 30 minutes. After the resultant mixture is concentrated under reduced pressure, the residue is dissolved in 100 ml of chloroform, dried over anhydrous magnesium sulfate, and then concentrated under reduced pressure to give 7 g of oil. The oily hydrazono compound is suspended in 100 ml of toluene and 3.8 g of acetic anhydride and 2.5 g of acetic acid are added thereto. After the mixture is refluxed under heating with stirring for 6 hours, the resultant mixture is concentrated under reduced pressure. A solution of the residue in 100 ml of chloroform is washed with an aqueous sodium hydrogencarbonate solution, dried over anhydrous magnesium sulfate and then concentrated under reduced pressure to give 7 g of oil. The oil is subjected to chromatography on silica gel and eluted with chloroform-methanol (100:1 to 100:3) solvent. The eluate of the objective fraction is concentrated under reduced pressure to give 2 g of 4-(2-chlorophenyl)-2-[2-(4-n-hexylphenyl)ethyl]-9-methyl-6H-thieno[3,2-f][1,2,4triazolo[4,3-a][1,4]diazepine.

EXAMPLE 13

4-(2-chlorophenyl)-2-[2-(4-isobutylphenyl)ethyl]-6,9-dimethyl-6H-thieno[3,2-f][1,2,4]triazolo[4,3-a][1,4]diazepine A suspension of 2 g of 5-(2-chlorophenyl)-7-[2-(4-isobutylphenyl)ethyl]-3-methyl-1,3-dihydro-2H-thieno[2,3-e]-1,4-diazepin-2-one, melting at 188°-191° C. and 1.04 g of Lawesson reagent in 37 ml of toluene is stirred at 40°-45° C. for an hour. The resultant solution is concentrated under reduced pressure, and the residue is subjected to chromatography on silica gel and then eluted with chloroform-methanol (100:1 to 100:2). The objective fraction is concentrated under reduced pressure to give 1.2 g of 5-(2-chlorophenyl)-7-[2-(4-isobutylphenyl)ethyl]-3-methyl-1,3-dihydro-2H-thieno[2,3-e]-1,4-diazepine-2-thione.

To a solution of 9.1 g of 5-(2-chlorophenyl)-7-[2-(4-isobutylphenyl)ethyl]-3-methyl-1,3-dihydro-2H-thieno[2,3-e]-1,4-diazepine-2-thione in 150 ml of tetrahydrofuran is added 3.1 g of 100% hydrazine hydrate under ice-cooling and the mixture is stirred at room temperature for 2 hours. After the tetrahydrofuran is distilled off under reduced pressure, the residue is dissolved in 200 ml of chloroform and the solution is dried over anhydrous magnesium sulfate. After separating by filtration, the filtrate is concentrated under reduced pressure. To the residue is added 50 ml of ethyl orthoacetate and the mixture is heated at 70°-72° C. for an hour. The mixture is concentrated under reduced pressure, and the residue is subjected to chromatography on silica gel and eluted with chloroform-methanol (100:1 to 100:3) solvent. The eluate of the objective fraction is concentrated and the residue is crystallized from isopropyl ether to give 4.3 g of 4-(2-chlorophenyl)-2-[2-(4-isobutylphenyl)ethyl]-6,9-dimethyl-6H-thieno[3,2-f][1,2,4]triazolo[4,3-a][1,4]diazepine as colorless crystals, melting at 129.5°-131.5° C.

Pharmaceutical preparations

[part(s) means part(s) by weight.]

(1) Tablets

A composition of 0.5 part of the compound of Example 1, 25 parts of lactose, 35 parts of crystalline cellulose and 3 parts of corn starch is mixed well, and kneaded with binder prepared by 2 parts of corn starch. The paste is passed through a 16 mesh sieve and dried in an oven at 50° C., and forced through a 24 mesh sieve. The powder thus obtained, 8 parts of corn starch, 11 parts of crystalline cellulose and 9 parts of talc are mixed well and the mixture was compressed with a punch into tablets containing 0.5 mg of active ingredient.

(2) 1% Powder

A composition of 1 part of the compound of Example 1 and 90 parts of lactose is mixed well and kneaded with binder prepared by a suitable amount of methylcellulose. The mixture was passed through a 16 mesh sieve and dried in an oven at 50° C. The dried granules were forced through 32 mesh sieve with pressure and mixed with a suitable amount of silicon dioxide to produce 1% powder.

Although the present invention has been adequately discussed in the foregoing specification and examples included therein, one readily recognizes that various changes and modifications may be made without departing from the spirit and scope of the present invention.

What is claimed is:

1. A thienotriazolodiazepine compound of the formula:

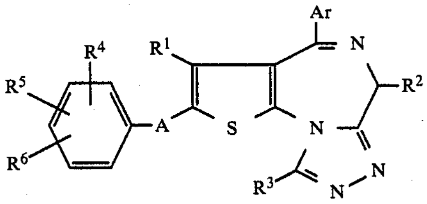

wherein Ar is pyridyl, phenyl or phenyl substituted by one to three substituents optionally selected from the group consisting of halogen, hydroxy, trifluoromethyl, straight or branched chain alkyl having 1 to 5 carbon atoms and straight or branched chain alkoxy having 1 to 5 carbon atoms, A is alkylene having 1 to 8 carbon atoms or alkylene having 1 to 8 carbon atoms substituted by straight or branched chain alkyl having 1 to 5 carbon atoms, $R^1$ is hydrogen or straight or branched chain alkyl having 1 to 5 carbon atoms, $R^2$ and $R^3$ are the same or different and each is hydrogen, trifluoromethyl or straight or branched chain alkyl having 1 to 5 carbon atoms, and $R^4$, $R^5$ and $R^6$ are the same or different and each is hydrogen, halogen, hydroxy, trifluoromethyl, straight or branched chain alkyl having 1 to 8 carbon atoms, straight or branched chain alkyl having 1 to 8 carbons atoms substituted by trifluoromethyl, straight or branched chain alkoxy having 1 to 8 carbon atoms, phenyl, phenoxy, aralkyl, aralkyloxy, or phenyl, phenoxy, aralkyl or aralkyloxy substituted by one to three substituents optionally selected from the group consisting of halogen, hydroxy, straight or branched chain having 1 to 5 carbon atoms, trifluoromethyl and straight or branched chain alkoxy having 1 to 5 carbon atoms on the aromatic ring, and pharmaceutically acceptable acid addition salts thereof.

2. The compound of claim 1 wherein Ar is pyridyl, phenyl or phenyl substituted by one to three substituents optionally selected from the group consisting of halogen, hydroxy, straight or branched chain alkyl having 1 to 5 carbon atoms and straight or branched chain alkoxy having 1 to 5 carbon atoms, A is alkylene having 1 to 8 carbon atoms or alkylene having 1 to 8 carbon atoms substituted by straight or branched chain alkyl having 1 to 5 carbon atoms, $R^1$ is hydrogen, $R^2$ and $R^3$ are the same or different and each is hydrogen or straight or branched chain alkyl having 1 to 5 carbon atoms, and $R^4$, $R^5$ and $R^6$ are the same or different and each is hydrogen, hydroxy, straight or branched chain alkyl having 1 to 8 carbon atoms, straight or branched chain alkoxy having 1 to 8 carbon atoms, phenyl, phenoxy, aralkyl, aralkyloxy, or phenyl, phenoxy, aralkyl or aralkyloxy substituted by one to three substituents selected from the group consisting of halogen, straight or branched chain alkyl having 1 to 5 carbon atoms, and straight or branched chain alkoxy having 1 to 5 carbon atoms on the aromatic ring, and pharmaceutically acceptable acid addition salts thereof.

3. A compound of claim 1 selected from the group consisting of 4-(2-chlorophenyl)-2-[2-(4-isobutylphenyl)ethyl]-9-methyl-6H-thieno[3,2-f][1,2,4]triazolo[4,3-a][1,4]diazepine, 4-(2-chlorophenyl)-2-[2-(4-methylphenyl)ethyl]-9-methyl-6H-thieno[3,2-f][1,2,4]triazolo[4,3-a][1,4]diazepine, 4-(2-chlorophenyl)-2-[4-(4-isobutylphenyl)butyl]-9-methyl-6H-thieno[3,2-f][1,2,4]triazolo[4,3-a][1,4]diazepine, 4-(2-chlorophenyl)-2-[2-(4-methoxyphenyl)ethyl]-9-methyl-6H-thieno[3,2-f][1,2,4]triazolo[4,3-a][1,4]diazepine, 4-(2-chlorophenyl)-2-[2-(4-n-butylphenyl)ethyl]-9-methyl-6H-thieno[3,2-f][1,2,4]triazolo[4,3-a][1,4]diazepine, 4-(2-chlorophenyl)-2-[2-(4-phenylphenyl)ethyl]-9-methyl-6H-thieno[3,2-f][1,2,4]triazolo[4,3-a][1,4]diazepine, 4-(2-chlorophenyl)-2-(2-phenylethyl)-9-methyl-6H-thieno[3,2-f][1,2,4]triazolo[4,3-a][1,4]diazepine, 4-(2-chlorophenyl)-2-(4-isobutylbenzyl)-9-methyl-6H-thieno[3,2-f][1,2,4]triazolo[4,3-a][1,4]diazepine, 4-(2-chlorophenyl)-2-[3-(4-isobutylphenyl)propyl]-9-methyl-6H-thieno[3,2-f][1,2,4]triazolo[4,3-a][1,4]diazepine, 4-(2-chlorophenyl)-9-ethyl-2-[2-(4-isobutylphenyl)ethyl]-6H-thieno[3,2-f][1,2,4]triazolo[4,3-a][1,4]diazepine, 4-(2-chlorophenyl)-2-[2-(4-isobutylphenyl)ethyl]-6,9-dimethyl-6H-thieno[3,2-f[1,2,4]triazolo[4,3-a][1,4]diazepine and 4-(2-chlorophenyl)-2-[2-(4-n-butylphenyl)ethyl]-6,9-dimethyl-6H-thieno[3,2-f][1,2,4]triazolo[4,3-a][1,4]diazepine.

4. A pharmaceutical composition for the prevention or treatment of various PAF-induced diseases comprising a therapeutically effective amount of the compound of claim 1 and a pharmaceutically acceptable carrier.

5. A method for the prevention or treatment of various PAF-induced diseases which comprises administering a therapeutically effective amount of at least one compound of claim 1 or a pharmaceutically acceptable acid addition salt thereof.

* * * * *